United States Patent [19]

Johnson, Jr. et al.

[11] Patent Number: 5,466,250

[45] Date of Patent: * Nov. 14, 1995

[54] AUTOMATIC FLUID COMPRESS AND CIRCULATING SYSTEM

[75] Inventors: Glenn W. Johnson, Jr., Summit; Henry J. McVicker, Chatham, both of N.J.

[73] Assignee: Aircast, Inc., Summit, N.J.

[*] Notice: The portion of the term of this patent subsequent to Jul. 27, 2010, has been disclaimed.

[21] Appl. No.: 109,382

[22] Filed: Aug. 19, 1993

Related U.S. Application Data

[63] Continuation-in-part of Ser. No. 737,402, Jul. 29, 1991, Pat. No. 5,230,335, which is a continuation-in-part of Ser. No. 644,835, Jan. 23, 1991, Pat. No. 5,314,455, and a continuation-in-part of Ser. No. 968,287, Oct. 29, 1992, abandoned.

[51] Int. Cl.$^6$ ........................................... A61F 7/00
[52] U.S. Cl. ............................. 607/104; 607/108; 601/15
[58] Field of Search ...................................... 607/104, 105, 607/107, 108, 109–112, 114; 601/15, 148–152; 165/46

[56] References Cited

U.S. PATENT DOCUMENTS

| | | |
|---|---|---|
| 1,732,380 | 10/1929 | Sarason. |
| 2,026,747 | 1/1936 | Nemzek. |
| 2,832,336 | 4/1958 | Davis et al.. |
| 3,403,673 | 10/1968 | MacLeod. |
| 3,548,819 | 12/1970 | Davis et al.. |
| 3,633,567 | 1/1972 | Sarnoff. |
| 3,683,902 | 8/1972 | Artemenko et al.. |
| 3,862,629 | 1/1975 | Rotta. |
| 3,871,381 | 3/1975 | Roslonski. |
| 3,901,225 | 8/1975 | Sconce. |
| 3,942,518 | 3/1976 | Tenteris et al.. |
| 4,139,004 | 2/1979 | Gonzalez, Jr.. |
| 4,149,529 | 4/1979 | Copeland. |
| 4,197,837 | 4/1980 | Tringali et al.. |
| 4,335,726 | 6/1982 | Kolstedt. |
| 4,338,944 | 7/1982 | Arkans. |
| 4,407,276 | 10/1983 | Bledsoe. |
| 4,628,932 | 12/1986 | Tampa. |
| 4,688,572 | 8/1987 | Hubbard et al.. |
| 4,872,448 | 10/1989 | Johnson, Jr.. |
| 4,951,665 | 8/1990 | Schneider. |
| 4,962,761 | 10/1990 | Golden. |
| 4,964,402 | 10/1990 | Grim et al.. |
| 5,074,285 | 12/1991 | Wright. |
| 5,080,089 | 1/1992 | Mason et al.. |
| 5,172,689 | 12/1992 | Wright. |
| 5,230,335 | 7/1993 | Johnson, Jr. et al. ................... 607/108 |

OTHER PUBLICATIONS

"Hot/Ice Dual Function Equipment Model HE 500" product brochure, Thermotemp, Inc., Tampa, Fla.

N. Mindrebo et al.: Methodist Sports Medicine, date and page numbers unknown–"Knee Pressure Dressings and Their Effects on Lower Extremeity Venous Capacitance and Venous Outflow".

"Polarcare Cold Therapy" product brochure, BREG, Vista, Calif.

(List continued on next page.)

*Primary Examiner*—Mark S. Graham

[57] ABSTRACT

A thermal compress cuff for treating an injured knee has a fluid impervious chamber of flexible material with an upper transverse portion and depending arms extending from the transverse portion. The transverse portion is adapted to encompass a portion of a limb above the knee and the depending arms are adapted to encompass the limb along the sides of the knee and a portion of the limb below the knee while exposing the patella of the knee. The chamber is adapted to receive and contain a thermal fluid for abutting contact with the encompassed portion of the limb and the chamber further contains a plurality of tethers to constrict the amount of thermal fluid which may enter the cuff. In addition, the cuff is provided with elastic straps which hold the cuff on to the knee and allow compression to be exerted on the suprapatellar region of the knee while limiting the pressure exerted on the distal and popliteal areas of the leg.

29 Claims, 3 Drawing Sheets

OTHER PUBLICATIONS

J. P. Sloan et al.: vol. 16, No. 8, Aug. 1988, *The Physician and Sportsmedicine*—"Effects of Cold and Compression on Edema".

B. T. Cohn et al.: 0363-5465/89/1703-0344, vol. 17, No. 3—*The American Journal of Sports Medicine*—"The Effects of Cold Therapy in the Postoperative Management of Pain in Patients Undergoing Anterior Cruciate Ligament Reconstruction".

Letter dated Jun. 5, 1990, from Methodist Sports Medicine Center, regarding "Post-surgical Use of the CRYO–CUFF™ Knee Compression Dressing".

Committee on Complications of Arthroscopy Association of North America: *Arthroscopy: The Journal of Arthroscopic and Related Surgery*, vol. 1, No. 4, 214–200 (1985)—"Complications of Arthroscopy and Arthroscopic Surgery: Results of a National Survey".

An Aircast Incorporated Bulletin relating to the Aircast Cryo–Cuff™, a prior art device of the instant assignee.

*Podiatric Products*, Jul. 1990, p. 14, "3K Cryotherapy Compression Bandage".

Advertisement of PI Medical, copyright 1990, "$CP_2$ Therapy Cold and Pressure Cold Pad".

"Interview of Dr. Kenneth L. Knights," *Orthopedic and Sports Medicine News*, pp. 1–5, date unknown.

M. S. Stringer et al.: Bone Joint Surg [BR] 189; 71–B: 492–7—*Deep Vein Thrombosis After Elective Knee Surgery*.

Husni E., Ximines J, Hamilton F: *Pressure Bandagin of the Lower Extremity, Use and Abuse*. JAMA 206:2715–2718, 1968.

Duffley H, Knight K: *Ankle Compression Variability Using the Elastic Wrap with a Horseshoe, Edema II Boot, and Air–Stirrup Brace*, Athletic Training 24:320–323, 1989.

Mindrebo N, Shelbourne D: *Knee Pressure Dressings and Their Effects on Lower Extremity Venous Capacitance and Venous Outflow*, Methodist Sports Medicine Center, Indianapolis, Ind. 1989 (unpublished).

Effect of the Cryo/Cuff™ Knee Compression Dressing and an Elastic Wrap on Swelling of the Calf (Aircast study).

AUTOMATIC FLUID COMPRESS AND CIRCULATING SYSTEM

This is a continuation-in-part application of U.S. Ser. No. 737,402 filed Jul. 29, 1991, U.S. Pat. No. 5,230,335, which is a continuation-in-part application of U.S. application Ser. No. 644,835 filed Jan. 23, 1991, U.S. Pat. No. 5,314,455, and a continuation-in-part application of U.S. application Ser. No. 968,287, filed Oct. 29, 1992, now abandoned.

FIELD OF THE INVENTION

The present invention relates to a simplified automatic apparatus for treating bodily injuries and ailments and in particular to an improved pump system apparatus for circulating fluid between a fluid source of predetermined temperature and a hollow body compress to apply compression and a high or low temperature fluid to the affected area.

The invention specifically includes an improved tethering system to restrict the amount of fluid allowed into the hollow body compress and an improved strap for securing the hollow body compress to a mammal's limb.

BACKGROUND OF THE INVENTION

Therapeutic advantages of the application of intermittent compression to injured or afflicted areas of the body to prevent venous stasis and reduce the risk of emboli are well recognized by the medical profession today. However, the automatic systems available for such purposes tend to be bulky, expensive, and allow limited mobility of the patient during use. It is also well known that the application of cold and compression following injury or certain surgery is beneficial.

Present devices available for such purposes generally require manual pumping or movement of the chilled fluid from its source to recycle the fluid as it is warmed at the body interface. During such recycling, there is a concomitant deviation of pressure, thus, in effect, rendering the process less efficient than desired. Moreover, in certain instances, for example, when the compress device is applied to a shoulder, additional help is required to cycle the system. In addition, with these devices additional compression is sometimes applied with an elastic wrap over the cold device. In this event, the amount of compression is unknown, and may be excessive, and the applied compression is static rather than intermittent or pulsating as preferred.

In commonly assigned copending application Ser. No. 737,402, filed Jul. 29, 1991, the therapeutic value of simultaneous application of cold and compression to an injured body part such as a knee is set forth. The invention disclosed therein, sold by the common assignee under the name "Aircast Cryo/Cuff", provides a simple and economical device that applies therapeutic cold and a first level of compression to the limited area of the knee that needs the therapy while using means for controlling the compression below the knee to a second predeterminable amount to minimize the constriction of venous circulation in the lower leg.

That invention includes a cuff-shaped compress with a watertight inflatable chamber shaped to envelope the anterior and sides of the knee including particularly the suprapatellar pouch and the area of the knee just below the patella. Those are the areas where posttrauma body fluids accumulate and where cold and compression are most needed. The cuff is economically fabricated from sheets of flat material and its novel design permits adjustable shaping so as to conform to the knee even when the knee and cuff are flexed at different angles. The cuff is held in place with an upper proximal strap and a lower distal strap that avoid the popliteal area and minimize constriction. When the cuff is applied to the knee, the straps are secured but not tightened. A first amount of compression is then supplied to the knee by inflating the cuff to a reasonably predeterminable amount which causes the cuff chamber to expand. The expansion tensions the straps and applies compression to the areas of the knee under the chamber.

The cuff normally is wrapped in place when empty and is then inflated with ice water which is supplied by a tube or fluid conduit from a cooler or container that is elevated above the cuff and the cuff is pressurized by gravity. With this technique, the amount of compression is determined by the elevation of the container above the cuff.

With such a device, chilled water becomes warm as it remains in contact with the body through the body/compress interface during treatment. Conversely, high temperature fluids are cooled as time passes. Thus, the effectiveness of both high and low temperature fluid treatments diminishes with time. Periodically, the fluid must be drained from the device and a fresh supply of fluid must be added.

The water from the cuff is routinely recycled back to the cooler for rechilling by lowering the cooler below the cuff. During the time required for rechilling the water, the pressure in the cuff falls and this permits even any minimal pooling of blood that might occur in the veins to be flushed out.

U.S. Pat. No. 5,080,089 attempted to remedy this problem of varying temperature at the cuff/body interface by providing an apparatus which, in one mode, allowed nonambient temperature fluid from a remote reservoir to be continuously circulated under pressure through a cuff wrapped around the injury. In another mode, air at ambient temperature is placed under pressure in the cuff and the cuff is sealed to apply compression, but not cold, to the limb. This has the advantage of near constant temperature without having to raise and lower the cooler periodically to recycle the water. However, the system is rather complicated and utilizes complex components, and is incapable of applying simultaneous compression and cold.

It is thus an object of the present invention to overcome the disadvantages of the prior art by providing an improved cuff which provides a high degree of compression in the proximal area over the suprapatellar pouch yet still minimizes constricting pressure in the distal and popliteal areas.

SUMMARY OF THE INVENTION

The present invention relates to a device defining a substantially inverted U-shaped hollow chamber having first and second walls for applying a therapeutic fluid cold and compression to the general area of the suprapatellar pouch and the general area alongside the knee. The device further includes compression controlling means forming part of the hollow chamber for providing generally concurrently a first level of compression to the general area of the leg alongside and below the knee, a second higher level of compression to the general area of only the suprapatellar pouch, and a third level of compression at the back of the leg opposite the suprapatellar pouch that is significantly less than the second level of compression applied to the suprapatellar pouch.

The instant invention also relates to a system for the circulation of chilled or other fluids through a fluid conduit between a fluid container and the hollow body compress, the system comprising a connector in the container, a motor driven air pump coupled to the connector and the container, and a timer coupled to the air pump motor to cause the air pump to cycle ON and OFF for predetermined periods of time, a means to depressurize the container, such that during the ON cycle the container is pressurized and fluid is forced from the container into the compress and during the OFF cycle fluid is allowed to flow back to the container from the compress.

In the preferred embodiment of the present system, the compress is first applied to the injured body part and then filled with chilled fluid, and the container is placed at a desired level with respect to the compress to put the compress under pressure. Intermittent pneumatic pressure is then automatically applied to the fluid, preferably by utilizing a simple and inexpensive air pump coupled to the fluid container to pressurize the container in a cyclical fashion at predetermined intervals. A timer is coupled to the air pump to operate the motor in the desired intervals. Typically, the air pump is ON for 30 seconds and then OFF for 30 seconds.

During the ON cycle, the increased air pressure in the container forces a few ounces of chilled water from the container to the compress. During the OFF cycle, the air pressure is allowed to return to normal and a few ounces of warmed water return from the compress to the container.

To relieve the air pressure during the OFF cycle, a conventional solenoid operating air valve could be used. But this requires the cost and complexity of an extra component in the electrical circuit.

A surprisingly simple and effective alternative is to provide a continuous control air bleed in the system, where the bleed is large enough to permit relief of the pressure during the OFF cycle, and small enough to permit the desired level of pressurization during the ON cycle. It has been found that a bleed orifice in range of about 0.020 to 0.025 inch will meet these requirements when used with a small economical vibratory air pump of the type commonly used to aerate aquariums, such as a pump having a flow rate of about 1000–1500 cc/min and an output air pressure of about 0.1–0.35 $kg/cm^2$. A more powerful pump would, of course, require the use of a larger orifice. A variable size bleed orifice can also be used. The orifice may be installed at the pump unit.

The cyclical flux of pressure, and flow of fluid to and from the compress also causes oscillating compression between the compress and limb. The amount of compression is a function of the elevation of the container in relation to the compress. For example, with the pump as described above operating on a one-gallon container about 12 inches high, and with the top of the container level with the top of the compress, the compress/leg pressure oscillates between about 5-to-15 mmHg. When the top of the container is about 8 inches above the compress, the pressure oscillates between about 15-to-35 mmHg.

Because the fluid flows back and forth from container to compress, only a single connecting fluid conduit is required, instead of the dual tubes used in conventional recirculating systems. The conduit is preferably covered with an insulating sleeve to maintain the low temperature of the fluid. When the system is used with ice water as the circulating fluid, the skin temperature under the compress falls rapidly to the 50° F. range. If this is too cold, temperature can be regulated by turning a flow valve provided between the container and the compress. The cold is maintained as long as the ice in the container lasts, typically up to about 8 hours with a gallon container of ice water.

BRIEF DESCRIPTION OF THE DRAWINGS

These and other objects of the invention will be more fully disclosed in the following DETAILED DESCRIPTION when taken in conjunction with the drawings in which like numerals represent like elements and in which:

FIG. 7 is a diagrammatic representation of a preferred system incorporating the cuff of FIG. 1 in which a motorized air pump is driven cyclically by a timer to pressurize the fluid container to force fluid through the fluid conduit to the compress during the ON cycle and to allow the fluid to return through the conduit to the container during the OFF cycle.

DETAILED DESCRIPTION OF THE DRAWINGS

Although the description hereinafter will refer to chilled water as being the fluid transferred from the fluid container to the compress, it is to be understood that a warm fluid could also be transferred from the container to the compress and thus the terms "chilled water" and "warmed water" would be interchangeable herein insofar as the operation of the device is concerned. Further, while the invention is disclosed as being applied to a knee cuff type of compress, it could also be used in a compress for the ankle, leg, arm, shoulder, or other body part. Also, the commonly assigned and copending application Ser. No. 737,402, filed Jul. 29, 1991, application Ser. No. 644,835, filed Jan. 23, 1991, and application Ser. No. 968,287, filed Oct. 29, 1992 are herein incorporated by reference in their entirety.

Figure 1:
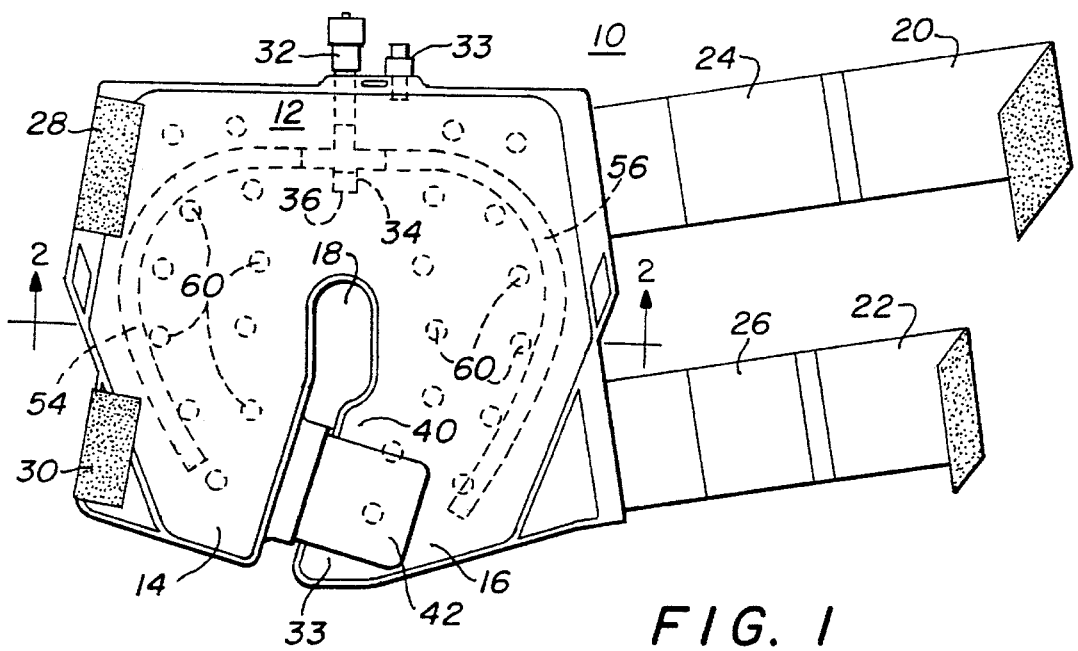
FIG. 1 is a top plan view of the preferred embodiment of the novel pressure cuff.
Figure 2:
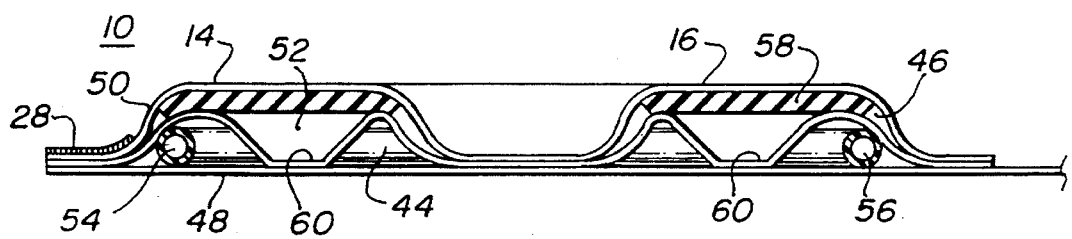
FIG. 2 is a cross-sectional view of the cuff shown in FIG. 1, taken in the direction of the arrows 2—2.

As can be seen in FIGS. 1 and 2, the preferred embodiment of the novel thermal compress device or cuff, designated generally by the numeral 10, is designed to be applied to a person's knee. Cuff 10 has an upper transverse portion 12 and lower depending arms 14 and 16 extending from upper portion 12. An opening designated by the numeral 18 in cuff 10 is intended to receive the kneecap or patella. In this way, pressure and temperature are not applied to the patella or kneecap of a person wearing compress 10. A proximal strap 20 and a distal strap 22 are attached to cuff 10 at tabs or wings 24 and 26, respectively, on arm 16. Straps 20 and 22 are made of any well-known flexible and elastic material having a portion with a fastening material such as hook-and-loop. Straps 20 and 22 are arranged for attaching relationship with mating hook-and-loop strips 28 and 30 mounted on arm 14 of cuff 10.

Cuff 10 further includes a connector 32 for admitting the cold liquid through a check valve 34 and outlet 36 to the interior of cuff 10.

It is noted that cuff 10 is bifurcated beginning at opening 18, thus separating depending arms 14 and 16. This permits adjustment for knee angle, and width. Arm 16 includes a truncated portion 38 which is deemed by sides of arm 16 and dashed line 40. Portion 38 allows the profile of cuff 10 to be changed from flat to conical for better confirmation of arms 14 and 16 to the leg when the knee is in a flexed position.

Hook-and-loop fasteners 28 and 30 and elastic straps 20 and 22 connect depending arms 14 and 16 together under (or behind) the leg while a strap 42 and a mating hook-and-loop strip (not shown) connect arms 14 and 16 together over the top of the leg. Thus the upper (proximal) and lower (distal) straps 20 and 22 are placed so as to avoid the popliteal area of the knee and minimize the constriction thereof. This construction permits bending adjustment of cuff 10 for different degrees of flexation from full extension of a knee to about 30°. Arms 14 and 16 could be permanently attached to each other with flexible connectors without providing for adjustment if desired. The use of the flexible and elastic straps 20 and 22 under the leg tends to limit the constriction of the leg and thus minimizes venous constriction at the back of the leg which is desirable during treatment.

FIG. 2 is a cross-sectional view of cuff 10. Cuff 10 includes a fluid impervious chamber formed so as to be divided into inner and outer generally coextensive compartments 44 and 46, respectively. Compartment 44 has an outer wall 48 and compartment 46 has an outer wall 50. Each of compartments 44 and 46 has a common inner wall 52. Inner compartment 44 is adapted for receiving and containing the thermal fluid in a desired temperature range in generally uniform and abutting contact via wall 48 with the encompassed portion of the leg being treated.

Internal syphoning tubes 54 and 56 connect to connector 32, as shown in FIG. 1, and are for draining the fluid from inner compartment 44. Draining is important for rechilling the fluid warmed by extended therapy. Tubes 54 and 56 are, preferably, formed of a material such as plastic and are approximately 5/16 inch in diameter. They extend from connector 32 to the distal end of each of arms 14 and 16. Thus, even though connector 32 is at the top of compress 10, all of the fluid can be completely drained from the bottom.

An open-cell urethane foam material 58, which is preferably 0.30 inch thick, compresses to about half its normal thickness under a 1 psi load. This urethane foam is suitable for use in outer compartment 46 for insulating the underlying inner compartment 44 to minimize sweating while maintaining the shape of cuff 10. When cuff 10 is used, proximal strap 20 and distal strap 22 secure cuff 10 to the leg snugly. Cuff 10 may then be pressurized with a fluid from an elevated container using a closed cycle system.

Figure 3:
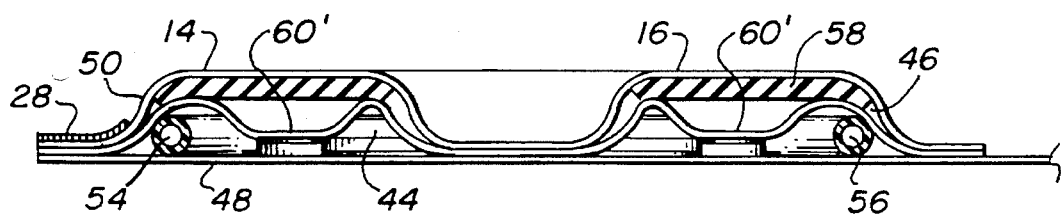
FIG. 3 is a cross-sectional view of an alternate embodiment of the cuff shown in FIG. 1, taken in the direction of the arrows 2—2.

In order to optimize the pressure exerted on the proximal area over the suprapatellar pouch and minimize constricting pressure in the distal and popliteal areas, elastic straps 20 and 22 are used in conjunction with a plurality of tethering dimples 60 which are shown in FIGS. 1 and 2. Tethering dimples 60 are added throughout both the proximal and distal areas of cuff 10 in order to restrict expansion. This tethering reduces the volume of a filled cuff 10 by about 40%, typically from about 900 g untethered to 550 g of water tethered. Tethering dimples 60 are created by spot welding the two sides 48 and 52 of the chamber as illustrated in FIG. 2. An alternative, shown in FIG. 3, is to weld a short tethering strap 60' to each internal surface 48 and 52 to permit some but limited expansion in the immediate area.

Figure 4:
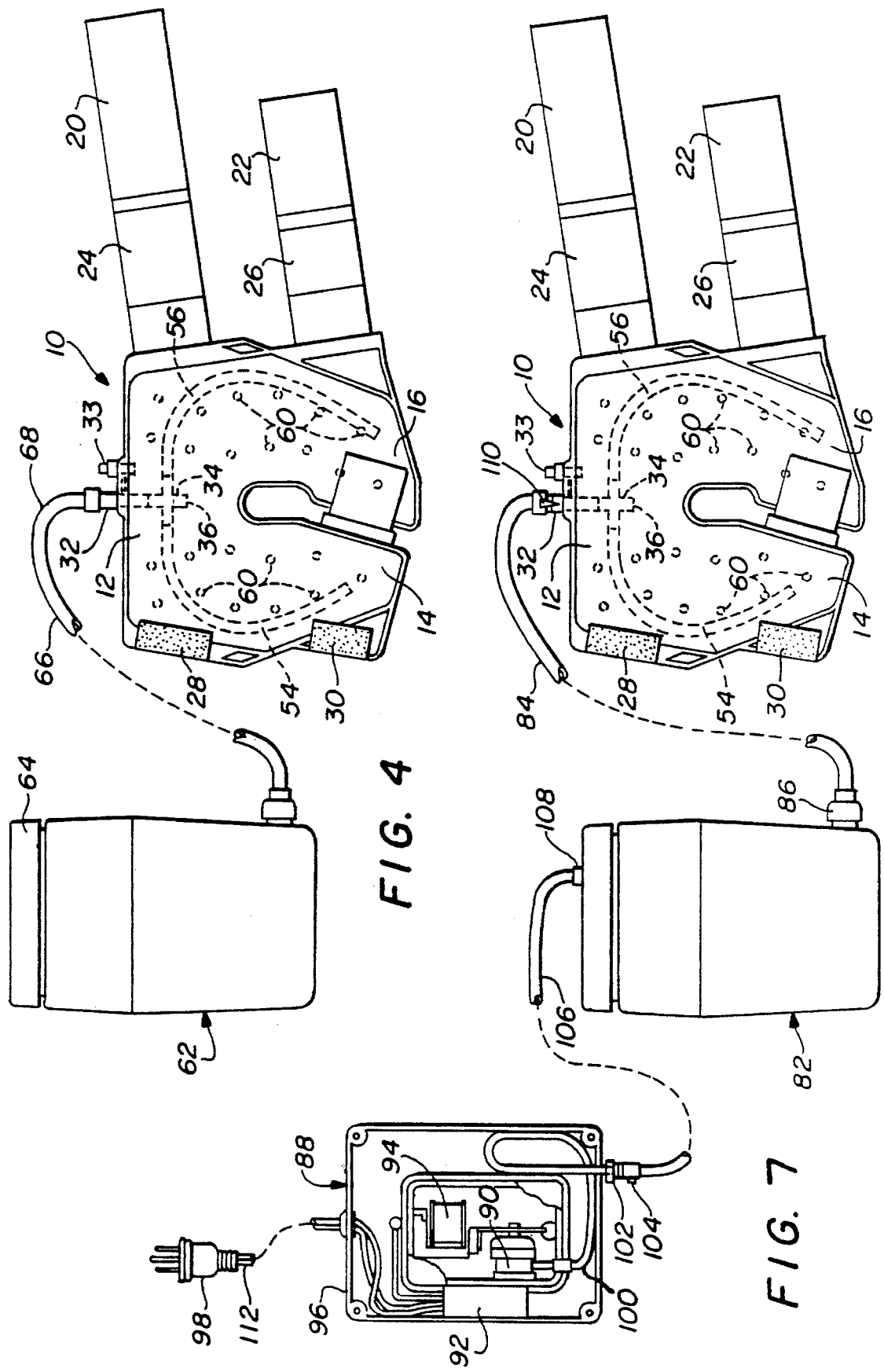
FIG. 4 is a diagrammatic representation of a novel pressure cuff in conjunction with a fluid container which forces fluid through a fluid conduit to the compress by elevating the fluid container above the compress to allow gravity to force fluid into the compress.

As shown in FIG. 4, a cooler container 62, which may be either a flexible pouch or a rigid container, holds a fluid such as ice and water sufficient for preferably six to 8 hours of Cryotherapy. Cooler 62, if a rigid container, has a lid 64 and is coupled by a hose 66 to connector 32 of cuff 10. After cuff 10 is applied to the leg, cooler 62 is elevated above the limb and the ice-chilled water flows into cuff 10. Compression of the limb, due to the gravity flow of the ice water is proportional to the elevation of cooler 62 with respect to cuff 10. A manually operated valve 68 allows flow of ice water to be stopped when the desired pressure is reached by manually closing valve 68. Thus, the pressure is sealed in cuff 10 and the skin temperature falls rapidly.

After 15 to 30 minutes, body heat will warm the water in cuff 10. The water is then "rechilled" by reversing the cycle. Cooler 62 is lowered below the leg and valve 68 is open. The warm water then drains through tubes 54 and 56 back into cooler 62. After a short interval allowing mixing of the water with the ice, cooler 62 is again elevated and the cuff-filling process repeated. Thus, a closed, chilled water system can be used and the waters recirculated between container 62 and cuff 10 to maintain the water at a desired temperature. As previously pointed out, tubes 54 and 56 extend to the distal areas of inner compartment 44 of arms 14 and 16, thus draining the warm water from all of compartment 42. When filling inner compartment 44 with cold water, a vent 33 may be opened to allow air to escape as the chilled water is entering compartment 44.

As thermal fluid fills inner compartment 44 it expands cuff 10, compresses the user's leg, and tightens straps 20 and 22. Normally, cuff 10 will expand uniformly around the upper and lower limb. Because most of the swelling after knee surgery takes place in the suprapatellar pouch (immediately above the knee), it is medically desirable to have more cold and compression in the proximal area above the patella and less in the distal and popliteal areas covered by arms 14 and 16 and straps 20 and 22, respectively.

In order to provide more compression to the proximal area and less constriction in the distal and popliteal areas, the present invention includes means to restrict the amount of expansion of the fluid compartment throughout arms 14 and 16 and transverse area 12. In addition, straps 20 and 22 are made of an elastic material which expands as cuff 10 is filled and compression is exerted on the leg.

It has been found that with interior cruciate ligament reconstruction, a portion of the patella tendon is often harvested, along with a plug of bone from its site of insertion into the tibia. This localized wound just below the patella is painful and a source of bleeding and swelling. Therefore, the area just below the patella also desirably requires cold and compression. As shown in FIG. 1, triangular cuff section 38 supplies cold and some moderate degree of compression to the area in front of the leg just below the patella of the knee. Triangular cuff section 38 also has a tethering dimple 60 to restrict the amount of fluids entering therein and thus controlling the amount of pressure that can be applied to the area in front of the knee and below the patella.

Figure 5:
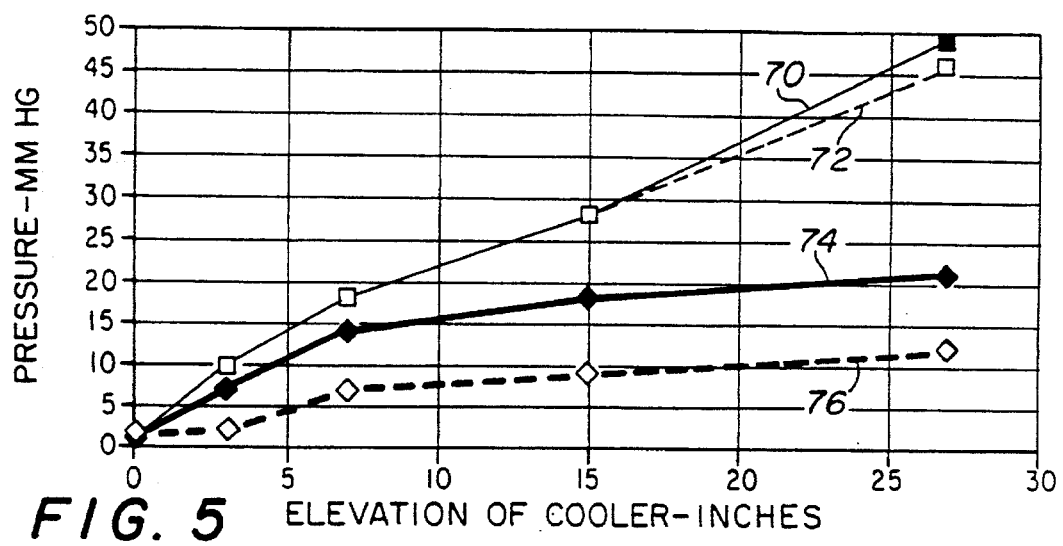
FIG. 5 is a graphic representation showing the difference in pressures exerted by the cuff on the suprapatella and the distal and popliteal areas of the knee.
Figure 6:
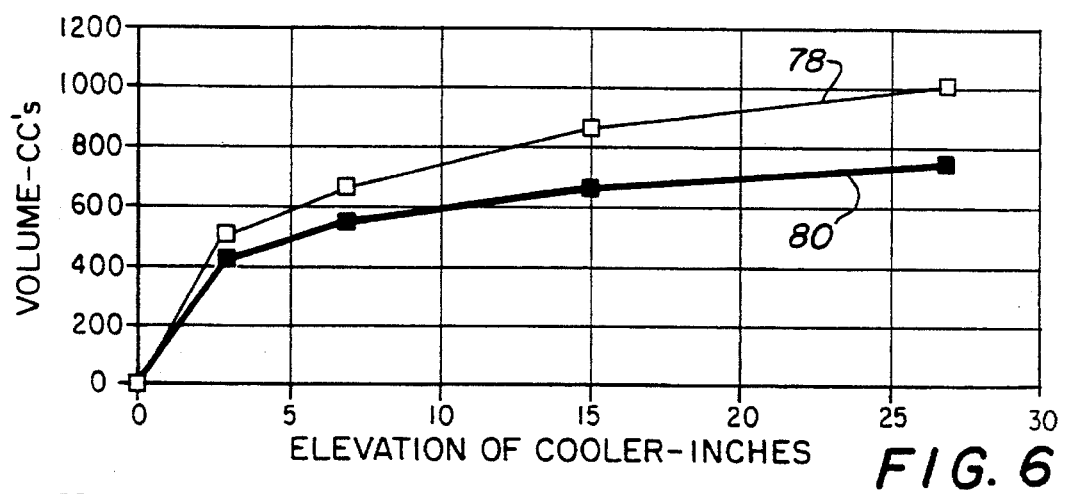
FIG. 6 is a graphic representation showing the improved pressures exerted on the suprapatellar region and the pressure exerted by an inelastic versus elastic strap.

The graph of FIGS. 5 and 6 demonstrates the advantages of the novel cuff system described in conjunction with FIG. 4. Referring to FIG. 5, line 70 is an indication of the pressure exerted on the suprapatellar region in millimeters of mercury versus the elevation of cooler 62 relative to cuff 10 when cuff 10 only has tethering dimples in arms 14 and 16 and strap 20 is inelastic. As can be seen, the pressure increases with the increase in the elevation of cooler 62. Line 72 is a graphic representation of the pressure exerted on the distal and popliteal areas by inelastic strap 20. The pressure exerted by inelastic strap 20 as indicated at line 72 represents constriction to the venous blood flow to the leg which it is medically desirable to minimize.

Lines 74 and 76 illustrate the novel advantages of the disclosed cuff 10. As can be seen from line 74, the pressures exerted on the suprapatellar region increase significantly less with a plurality of tethers 60 throughout arms 14 and 16 in transverse region 12 in combination with an elastic strap 20. This is a medically advantageous result as it helps minimize the possibility of overpressurization of the suprapatellar region by elevating cooler 62 too high. Line 76, when compared to line 72, further illustrates an advantage of using a plurality of tethers 60 in combination with an elastic strap 20 by showing a significant decrease in the pressure exerted on the distal and popliteal areas of a treated leg. Hence, by using a combination of the disclosed tethers 60 and an elastic strap 20, a sufficient pressure can be exerted on a suprapatellar region while having the advantageous effect of significantly reducing the constricting pressures on the distal and popliteal areas to allow the continuation of venous blood flow in the leg.

FIG. 6 is a graphic example of the reduction in volume of cuff 10 by the addition of tethers 60. Line 78 shows a typical fluid volume of a cuff such as that shown in commonly assigned and copending application Ser. No. 737,402, filed Jul. 29, 1991. Line 80 shows a typical volume of fluid for novel cuff 10 of the present invention. This significant reduction in fluid volume is one of the factors in reducing the pressures on the suprapatella in distal and popliteal areas of the leg.

FIG. 7 is a diagrammatic representation of an alternative embodiment of the present invention. In FIG. 7, a fluid container 82 is coupled to compress 10 with a fluid conduit 84 and connectors 86 and 32. Cuff 10 is a cuff as described in FIG. 1 above.

FIG. 7 includes pump unit 88 having an air pump 90, an electrical timer 92, and a motor 94 in a common housing 96 that can be plugged into a wall socket by means of a plug-in-type terminal 98. Air pump 90 is a standard vibratory air pump such as that used in aquariums and may be manufactured by Eiko Electric in Taiwan. Timer 92 is a timer of a type well known in the art such as those manufactured by Control Products Corp. in Grafton, Wis. Timer 92 is preferably solid-state and may be arranged to have a desired duty cycle. A preferred duty cycle useful in the instant invention is 30 seconds ON and 30 seconds OFF. Thus, motor 94 is turned ON for 30 seconds and pump unit 88 pumps air through hose 100 within pump unit 88 to connector 102 having bleed valve 104 and through external air hose 106 to connector 108 of container 82. As motor 94 runs for 30 seconds, it causes pump 90 to pressurize container 82, thus forcing a predetermined volume of chilled fluid through connector 86, conduit 84, and connector 32 to check valve 34 and the interior of compress 10. A fluid flow control valve 110 in connector 32 may be used to control the amount of fluid flowing from conduit 84 into compress 10 to prevent overcooling by restricting fluid flow into compress 10.

The increased flow of water into compress 10 also increases compression on the limb in contact with compress 10 during the ON cycle, and the compression falls as the water returns to container 82 during the OFF cycle. When the top of container 82 is about the same elevation as compress 10, the pressure oscillates between about 5-to-15 mmHg above atmospheric pressure. When the top of container 82 is about 8 inches above compress 10, the pressure oscillates between about 15-to-35 mmHg above atmospheric pressure. Thus, the system provides a continuous application of cold, as well as oscillating compression of a predictable and adjustable magnitude.

The system is also surprisingly simple, economical, and safe. There are no moving pans other than the vibratory pump 90. Motor 94 is very small and uses very little power. The electricity is isolated to pump unit 88 having an electrical cord 112 that is connected to plug 98 which is plugged into a wall socket. Pump motor 94 and timer 92 typically draw only about 4 watts of power 50% of the time. All electrical components are isolated from the water-filled container 82 and compress 10 by air tube 106 that connects pump unit 88 to fluid container 82.

Because the water flows back and forth between container 82 and compress 10, only a single connecting conduit 84 is required with single connectors 86 and 32 to container 82 and compress 10, respectively. Within compress 10, the efficient exchange of cold water for warm may be enhanced by one-way check valve 34. Check valve 34 opens during the ON cycle to permit pressurized water to flow from container 82 into the top of compress 10, but closes during the OFF cycle and forces return of warmer water to container 82 through the ends of tubes 54 and 56, which extend substantially to the bottom of compress 10. This is facilitated by the short length of opening 36, a preferred fight angle connection of extension tubes 54 and 56 to the opening 36, and by surface tension resistance to fluid flow in extension tubes 54 and 56. Thus, as shown by the arrows in FIG. 7, cold water enters the top of compress 10 through one-way check valve 34 and warm water returns to container 82 from the bottom of compress 10 through the ends of tubes 54 and 56, through connector 32, conduit 84, and connector 86. This arrangement provides more uniform distribution of cold water and precludes accumulation of a pocket of warm water at the top of compress 10. The oscillating pressurization of fluid container 82 on a cyclical basis provides the necessary compression and decompression of compress 10.

Figure 8:
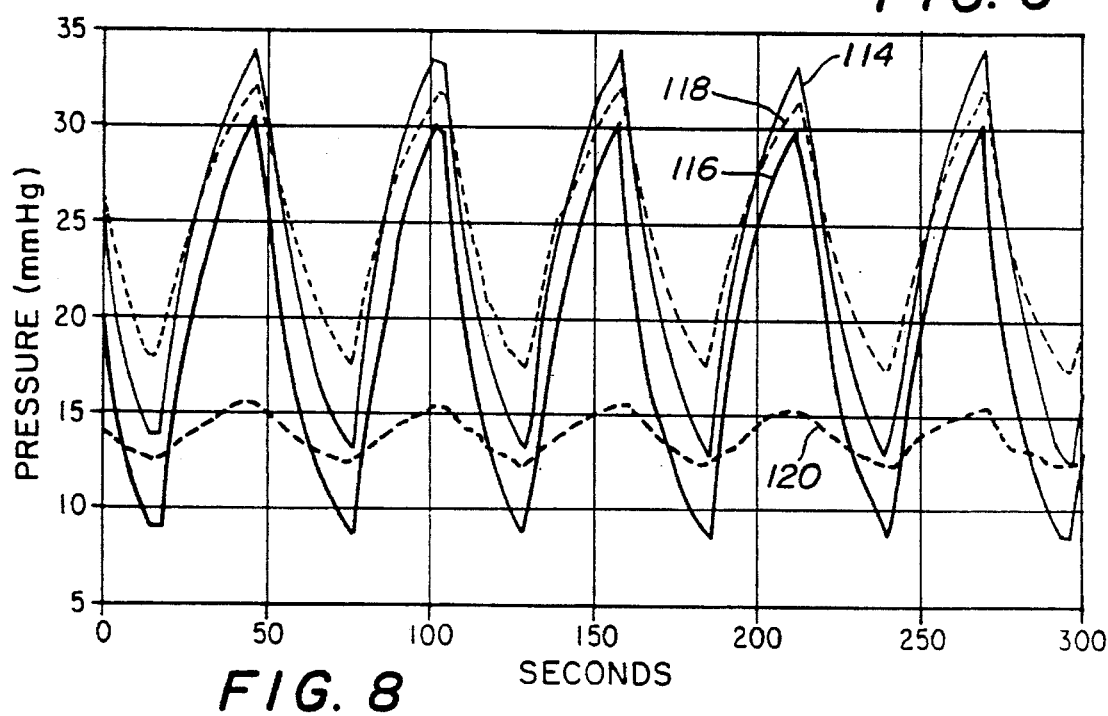
FIG. 8 is a graphic representation showing the reduced volume capacity of the novel pressure cuff.

FIG. 8 is a graphic representation of the advantage rendered from the novel cuff 10 in conjunction with the system disclosed in FIG. 7. Line 114 illustrates pressure exerted on the suprapatellar region by a prior art cuff which does not have sufficient tethering dimples 60 and that has an inelastic strap 20. When line 114 is compared with line 116, which discloses the pressures exerted by the novel cuff shown in FIG. 7, it can be seen that the pressure exerted on a suprapatellar region is only slightly diminished with the use of the novel cuff 10 disclosed herein. The novel and significant advantage of cuff 10 of the present invention can be easily seen when comparing line 118 with line 120. Line 118 discloses the pressure exerted on the distal and popliteal areas by an inelastic strap 20 of the prior art, which shows significant constriction to venous blood flow in the leg. However, when the combination of tethers 60 and an elastic strap 20 of the present invention are used, the pressure exerted on the distal and popliteal areas as shown by graph line 120 are significantly reduced. This allows adequate venous blood flow in the leg while still maintaining significant pressure as shown in line 116 on the suprapatellar pouch of the leg.

While the invention has been shown and described with respect to two particular embodiments thereof, this is for purposes of illustration rather than limitation; other variations and modifications of the specific embodiment herein shown and described will be apparent to those skilled in the art which are within the intended spirit and scope of the invention. Accordingly, the patent is not limited in scope in effect to the specific embodiments shown and described nor in any other way that is inconsistent with the extent to which the progress in the art has been advanced by the invention.

We claim:

1. A device for treating an injured knee of a leg comprising:

a substantially U-shaped hollow chamber having first and second walls and for applying therapeutic fluid cold and compression only to the general area of the suprapatellar pouch and the general area alongside the knee; and compression controlling means forming part of the hollow chamber for providing substantially simultaneously a first compression to the general area of the leg alongside and below the knee, a second, substantially higher level of compression to the general area of only the suprapatellar pouch, and a third level of compression at the back of the leg opposite the suprapatellar pouch that is significantly less than the second level of compression applied to the suprapatellar pouch.

2. A device as in claim 1 further including:

a transverse portion and first and second hollow depending arms forming said substantially U-shaped hollow chamber; and a hollow extension projecting inwardly from the distal end of at least one of the hollow arms for contacting the area between the arms adjacent and below the patella of the knee.

3. A device as in claim 2 wherein said hollow extension further comprises a hollow triangular section integrally formed with the distal end of one of the hollow arms in substantially superimposed relationship with the area adjacent and below the patella of the knee to allow cold and compression to be applied thereto.

4. A device as in claim 2 wherein said compression controlling means includes:

a first plurality of spaced tethers in each of the depending arms to limit the distance the first and second walls of the depending arms move apart and thus limit the volume of fluid in the depending arms to cause the first compression to the general area of the leg alongside and below the knee; and a first elastic strap for attaching said depending arms to said leg below the knee.

5. A device as in claim 4 wherein said compression controlling means further includes:

a second plurality of spaced tethers in the transverse portion of the hollow chamber for limiting the distance the first and second walls of the transverse portion can move apart such that if excessive pressure is applied to the hollow chamber, compression of the suprapatellar pouch is limited to the second level of compression, the second plurality of spaced tethers in conjunction with the first plurality of spaced tethers reducing the available liquid volume of the entire hollow chamber by approximately 40%; and a second elastic strap for attaching the transverse portion of the hollow chamber to the suprapatellar pouch such that, if excessive pressure is applied to the hollow chamber, the compression in back of the leg opposite the suprapatellar pouch under said second elastic strap is limited to the third level of compression that is less than the second level of compression.

6. A device for treating an injured knee of a leg comprising:

compress means for applying therapeutic fluid cold and compression only to the general area of the suprapatellar pouch and to the general area of the leg alongside the knee;

compression controlling means forming part of the compress means for applying simultaneously a first level of compression to the general area of the leg alongside and below the knee, a second significantly greater level of compression to the general area of only the suprapatellar pouch, and a third level of compression at the back of the leg opposite the suprapatellar pouch that is significantly less than the second level of compression applied to the suprapatellar pouch; and said compression controlling means including fastening means for attaching the compress means to the knee of the leg.

7. A device as in claim 6 wherein the compress means comprises:

a hollow liquid-tight chamber having inner and outer walls forming both a transverse portion and first and second hollow depending arms;

the transverse portion contacting the general area of only the suprapatellar pouch; and the first and second hollow arms extending generally along and in contact with the respective sides of the knee to form an open area between the arms.

8. A device as in claim 6 further including a hollow extension projecting inwardly from the distal end of at least one of the hollow arms for contacting the area between the arms adjacent and below the patella of the knee.

9. A device as in claim 7 wherein said compression controlling means includes:

a first plurality of spaced tethers in each of the depending arms to limit the distance the first and second walls of the depending arms move apart and thus limit the volume of fluid in the depending arms; and a first elastic strap providing at least a portion of said fastening means for attaching said compress means to the knee of the leg.

10. A cuff as in claim 9 wherein said compression controlling means further includes:

a second plurality of spaced tethers in the transverse portion of the hollow chamber for limiting the distance the first and second walls of the transverse portion can move apart such that, if excessive pressure is applied to the hollow chamber, compression of the suprapatellar pouch is limited to the second level of compression, the second plurality of spaced tethers in conjunction with the first plurality of spaced tethers reducing the available liquid volume of the entire hollow chamber by approximately 40%; and a second elastic strap for attaching the transverse portion of the hollow chamber to the suprapatellar pouch such that, if excessive pressure is applied to the hollow chamber, the compression in back of the leg opposite the suprapatellar pouch under said second elastic strap is limited to the third level of compression that is less than the second level of compression.

11. A thermal compress cuff for treating an injured knee of a limb, said device comprising:

a fluid impervious chamber formed of flexible material and having a transverse portion and arms depending from and substantially perpendicular to the transverse portion;

the transverse portion adapted to encompass a portion of the limb above the knee and the depending arms adapted to encompass at least a portion of the limb along the sides of and below the knee, said arms being separated to expose the patella of the knee;

said chamber being adapted for receiving and containing a thermal fluid for treatment of said knee and for abutting contact with the encompassed portion of the limb;

first strap means for holding the transverse portion of the chamber in encompassing engagement with the portion of the limb above the knee;

second elastic strap means for holding the depending arms of the chamber in encompassing engagement with at least a portion of the limb along the sides of and below the knee with the patella being positioned between the depending arms; and compression controlling means for causing the portion of said chamber encompassing the limb above the knee to limit the compression applied to the limb above the knee to a first level of compression and for causing a second level of compression to be applied to the limb along the sides of an below the knee that is significantly less than said first compression applied to the limb above the knee.

12. A thermal compress cuff as in claim 11 wherein at least a portion of said first strap is formed of elastic to cause a third level of compression to be applied to the back of the knee opposite the suprapatellar pouch that is significantly less than said first level of compression.

13. A thermal compress cuff as in claim 12 further comprising:

a common wall dividing the chamber into inner and outer compartments;

means coupled to the interior of the inner compartment for supplying a thermal fluid thereto, an outer surface of the inner compartment being adapted for abutting contact with the encompassed portion of the limb; and a resilient material contained in the outer compartment for insulating the underlying inner compartment and for maintaining the shape of the cuff while permitting confirmation of the cuff to the encompassed limb.

14. A thermal compress cuff as in claim 11 wherein said compression controlling means includes first expansion restricting means in the inner compartment in the transverse portion of the thermal compress cuff to restrict the amount of thermal fluid therein so as to limit the first level of compression applied to the limb above the knee if excessive pressure is applied to the inner compartment.

15. A thermal compress cuff as in claim 14 wherein the compression controlling means further includes second expansion restricting means in the inner compartment in the distal area of the arms to cause a lesser amount of restricted expansion than the restricted expansion in the transverse portion of the thermal compress cuff such that the second level of compression that is applied to the limb along the sides of and below the knee is significantly less than said first level of compression applied to the suprapatellar pouch.

16. A thermal compress cuff as in claim 14 wherein said transverse portion comprises first and second walls and said first expansion restricting means further includes:

a first plurality of spaced tethers in the transverse portion of the hollow chamber for limiting the distance the first and second walls of the transverse portion can move apart thus limiting the volume of fluid therein.

17. A thermal compress cuff as in claim 16 wherein said second expansion restricting means further includes:

a second plurality of spaced tethers in each of the depending arms to limit the distance the first and second walls of the depending arms move apart and thus limit the volume of fluid in the depending arms; and the second plurality of spaced tethers in conjunction with the first plurality of spaced tethers reducing the liquid volume of the entire hollow chamber by approximately 40%.

18. A thermal compress cuff as in claim 11 wherein said first strap is at least partially elastic so that the third level of compression in back of the leg opposite the suprapatellar pouch under said first strap is significantly less than the first compression applied to the suprapatellar pouch.

19. An automatic system for the application of a non-ambient temperature to the leg of a mammal, the system comprising:

a substantially U-shaped hollow chamber for applying therapeutic fluid cold and compression only to the general area of the suprapatellar pouch and the general area alongside the knee;

compression controlling means forming part of the hollow chamber for providing simultaneously a first compression to the general area of the leg alongside and below the knee, a second substantially higher level of compression to the general area of only the suprapatellar pouch, and a third compression at the back of the leg opposite the suprapatellar pouch that is significantly less than the second compression applied to the suprapatellar pouch;

first and second straps forming a part of the hollow chamber for attaching the cold and compression applying hollow chamber to the knee;

a fluid container in fluid communication with said hollow chamber;

a motor driven pump operatively coupled to said fluid container to provide pressurized air thereto; and cycling means coupled to the air pump motor to cause the air pump to cycle ON and OFF for predetermined periods of time such that during the ON cycle said air pump pressurizes said container to force fluid from said fluid container into said hollow chamber and, during the OFF cycle, fluid is allowed to flow back to the container from the hollow chamber.

20. A system as in claim 19 wherein said U-shaped hollow chamber comprises depending arms comprising first and second walls, and wherein said compression controlling means includes:

a first plurality of spaced tethers in each of the depending arms to limit the distance the first and second walls of the depending arms move apart and thus limit the volume of fluid in the depending arms; and said first strap for attaching said depending arms to said leg being at least partially elastic.

21. A system as in claim 20 wherein said U-shaped hollow chamber further comprises a transverse portion comprising first and second walls, and wherein said compression controlling means further includes:

a second plurality of spaced tethers in the transverse portion of the hollow chamber for limiting the distance the first and second walls of the transverse portion can move apart such that if excessive pressure is applied to said hollow chamber, compression of the suprapatellar pouch is limited to the second level of compression, the second plurality of spaced tethers in conjunction with the first plurality of spaced tethers reducing the liquid volume of the entire hollow chamber by approximately 40%; and said second strap for attaching the transverse portion of the hollow chamber to the suprapatellar pouch being at least partially elastic such that the compression in back of the leg opposite the suprapatellar pouch under said second strap is limited to the third compression that is significantly less than the second compression.

22. An automatic system for the application of a non-ambient temperature to a limb of a mammal, the system comprising:

a hollow body compress having inner and outer walls:

a transverse portion of said hollow body compress adapted to encompass substantially only the suprapatellar pouch above the knee;

first and second spaced arms depending from the transverse portion and adapted to encompass at least a portion of the limb along the sides of the knee, said arms being separated to accommodate the patella of the knee;

compression controlling means forming part of the hollow body compress for applying a first compression to the general area of the leg alongside the knee while simultaneously applying a second significantly greater level of compression to the general area of the suprapatellar pouch and for providing a third compression at the back of the leg opposite the suprapatellar pouch that is significantly less than the second compression applied to the suprapatellar pouch, said compression controlling means including fastening means for attaching the hollow body compress to the leg;

a fluid container;

a fluid conduit coupled between the fluid container and the hollow body for supplying said fluid thereto;

a motor driven air pump operatively coupled to said fluid container to provide pressurized air thereto; and cycling means coupled to the air pump motor to cause the air pump to cycle ON and OFF for predetermined periods of time such that during the ON cycle said air pump pressurizes the container to force fluid from said fluid container into said hollow body compress and, during the OFF cycle, fluid is allowed to flow back to the container from the hollow body compress.

23. A system as in claim 22 wherein said compression controlling means further includes:

first expansion restricting means in the inner and outer walls in the hollow arms to allow a first level of compression to be applied by the depending arms to the general area along each side of the knee in order to lessen venous constriction below the knee;

second expansion restricting means of the inner and outer walls in the transverse portion of the hollow body compress such that a second greater level of compression is allowed to be applied by the transverse portion to the suprapatellar pouch than the first level of pressure applied to the general area along each side of the knee by the depending arms of the hollow body compress; and an elastic strap associated with said compression controlling means for passing under the back of the leg opposite the suprapatellar pouch to enable the second level of compression applied to the general area of the suprapatellar pouch to be substantially greater than a third level of compression applied by the strap to the leg opposite the suprapatellar pouch.

24. A system as in claim 23 wherein the first and second expansion restricting means for restricting expansion of the inner and outer walls of the hollow arms and the transverse portion of the hollow body compress comprises:

attachment means in the distal area of each of the arms and in the transverse portion of the hollow body compress coupling the inner and outer walls to each other to limit the expansion of the hollow arms and the transverse portion of the hollow body compress by limiting the distance the inner and outer walls can move apart when fluid is inserted therein, said expansion limiting means creating the greater second level of compression in the general area of the suprapatellar pouch than the first level of compression applied by the depending arms to the general area along each said of the knee and reducing the available liquid volume of the entire hollow body compress by approximately 40%.

25. A system as in claim 24 wherein the attachment means coupling the inner and outer walls together in the area of the suprapatellar pouch and in the distal area of each of the arms comprises multiple spaced single tether strips coupling the inner and outer walls together to provide the appropriate restricted expansion of the hollow body compress in the areas of the suprapatellar pouch and the depending arms.

26. A system as in claim 24 wherein the attachment means coupling the inner and outer walls to each other comprises multiple spaced spot welded areas in both the area of the suprapatellar pouch and the depending arms for attaching the inner and outer walls together to provide the proper restricted expansion of the hollow body compress in the area of the suprapatellar pouch and the depending arms.

27. A system as in claim 22 further comprising:

a fluid flow control device coupled to said fluid conduit at a first location within said hollow body compress; and at least one extension tube extended from said fluid conduit to a second location within the hollow body compress remote from said first location such that, during the ON cycle of said motor drawn air pump, fluid forced into the hollow body compress enters through the fluid flow control device at the first location and, during the OFF cycle of said motor drawn air pump, fluid leaves the hollow body compress only through said extended tube from said second location to facilitate circulation of the fluid between the container and the hollow body compress over a period of time.

28. The system of claim 27 wherein said fluid flow control device is a one-way check valve.

29. A system as in claim 22 further comprising:

a first fluid flow control device positioned at a first location in the hollow body compress and coupled to said fluid conduit for allowing fluid flow only into the hollow body compress from the fluid container during the ON cycle of said air pump; and at least one extension tube extending from said fluid conduit to a second location in the hollow body compress remote from the first fluid flow control device for allowing fluid to flow out of the hollow body compress during the OFF cycle of said air pump such that fluid is forced from the fluid container through the connecting fluid conduit into the hollow body compress at said first location and fluid is forced from the hollow body compress back to the fluid container only from the second location in the hollow body compress during the cyclical ON and OFF pressurization.

* * * * *